US012558335B2

(12) United States Patent  (10) Patent No.: US 12,558,335 B2
Ahlenius et al.  (45) Date of Patent: Feb. 24, 2026

(54) **PREPARATION FOR REMOVAL AND/OR PREVENTION OF AN INFECTION ASSOCIATED WITH *STAPHYLOCOCCUS EPIDERMIDIS***

(71) Applicant: RLS GLOBAL AB, Mölndal (SE)

(72) Inventors: Mats Ahlenius, Mölnlycke (SE); Susanne Olausson, Lerum (SE); Gunilla Rudén, Askim (SE)

(73) Assignee: RLS GLOBAL AB, Mölndal (SE)

( * ) Notice: Subject to any disclaimer, the term of this patent is extended or adjusted under 35 U.S.C. 154(b) by 946 days.

(21) Appl. No.: 17/761,631

(22) PCT Filed: Sep. 18, 2020

(86) PCT No.: PCT/EP2020/076166
§ 371 (c)(1),
(2) Date: Mar. 18, 2022

(87) PCT Pub. No.: WO2021/053178
PCT Pub. Date: Mar. 25, 2021

(65) Prior Publication Data
US 2022/0339133 A1    Oct. 27, 2022

(30) Foreign Application Priority Data
Sep. 19, 2019    (SE) .................................. 1951058-5

(51) Int. Cl.
| *A61K 31/198* | (2006.01) |
| *A61K 33/14* | (2006.01) |
| *A61K 33/20* | (2006.01) |
| *A61K 33/24* | (2019.01) |
| *A61K 47/10* | (2017.01) |
| *A61P 31/04* | (2006.01) |

(52) U.S. Cl.
CPC ............ *A61K 31/198* (2013.01); *A61K 33/14* (2013.01); *A61K 33/20* (2013.01); *A61K 33/24* (2013.01); *A61K 47/10* (2013.01); *A61P 31/04* (2018.01)

(58) Field of Classification Search
CPC ...... A61K 31/198; A61K 33/14; A61K 33/20; A61K 33/24; A61K 47/10; A61P 31/04
See application file for complete search history.

(56) References Cited

U.S. PATENT DOCUMENTS

| 9,999,605 B2 * | 6/2018 | Almhöjd | ................. A61P 27/16 |
| 2016/0310525 A1 * | 10/2016 | Almhöjd | ............. A61K 47/183 |

FOREIGN PATENT DOCUMENTS

| CN | 104961588 | 10/2015 | |
| EP | 0818207 | 1/1998 | |
| JP | 2002370953 A | 12/2002 | |
| WO | WO-2013032961 A1 * | 3/2013 | ................ C02F 1/50 |
| WO | WO 2014/01657 | 1/2014 | |
| WO | WO 2014/016157 | 1/2014 | |
| WO | WO2015086535 | 6/2015 | |

OTHER PUBLICATIONS

Ziln, PLoS One, 2017, 12(2) (Year: 2017).*
Burgers et al., Arch Oral Biol. Jul. 2012;57(7):940-7.
Froese K. L. et al., "Factors governing odorous aldehyde formation as disinfection by-products in drinking water", Water Research, Elsevier, vol. 33, No. 6, Apr. 1, 1999.
Widerström et al., Journal of Clinical Microbiology, vol. 54, No. 7, pp. 1679-1681.
International Search Report and Written Opinion were mailed on Sep. 21, 2020 by the International Searching Authority for International Application No. PCT/EP2020/067325 filed on Jun. 22, 2020 and published as WO 2020/260191A1 (Applicant—Molnlycke Health Care AB) (16 pages).

* cited by examiner

*Primary Examiner* — Andrew D Kosar
*Assistant Examiner* — Phillip Matthew Rzeczycki
(74) *Attorney, Agent, or Firm* — Ballard Spahr LLP

(57)    ABSTRACT

Described is a method for treating or preventing an infection, such as an infection associated with *Staphylococcus epidermidis* such as a Health-Care Associated infection, a wound, a sore, an ulcer, a burn. The method includes applying a treatment preparation to a treatment site, the treatment preparation has a first component having a single amino acid, said single amino acid being leucine, and a second component having an active chlorine compound.

21 Claims, No Drawings

1

PREPARATION FOR REMOVAL AND/OR PREVENTION OF AN INFECTION ASSOCIATED WITH *STAPHYLOCOCCUS EPIDERMIDIS*

CROSS-REFERENCE TO RELATED APPLICATIONS

This application is a U.S. National Phase Application of International Application No. PCT/EP2020/076166, filed Sep. 18, 2020, which claims priority to Swedish Patent Application No. 1951058-5, filed Sep. 19, 2019, each of which are hereby incorporated by reference in its entirety.

TECHNICAL FIELD

The present disclosure relates to a kit of parts and a treatment preparation obtainable from said kit of parts which may be used in the treatment and/or prevention of an infection associated with *Staphylococcus epidermidis*.

BACKGROUND

*Staphylococcus epidermidis* (*S. epidermidis*) is a Gram-positive bacterium belonging to the genus *Staphylococcus*. It is part of the human flora such as the skin flora, and sometimes also the mucosal flora. Usually, *S. epidermidis* is not pathogenic. For instance, *S. epidermidis* in the normal skin is non-pathogenic. However, *S. epidermidis* has been reported to be pathogenic for people with compromised immune system, in skin lesion such as acne vulgaris and in Health-Care Associated Infections. Importantly, *S. epidermidis* has been found to be involved in biofilms on medical devices placed within the body of a patient which frequently leads to serious infections such as endocarditis and sepsis. Further, *S. epidermidis* may cause infections in wounds such as surgical wounds.

Journal of Clinical Microbiology, Volume 54, Number 7, pp. 1679-1681 discloses the significance of *S. epidermidis* in Health Care-Associated Infections. It is also disclosed that *S. epidermidis* is a common contaminant in clinical cultures, which poses a diagnostic challenge.

Unfortunately, treatment and/or prevention of infections associated with *S. epidermidis* is/are often ineffective due to decreased metabolic activity of bacteria associated with biofilms involving *S. epidermidis* making them resistant to antibiotics. Further, there is a general awareness that the use of antibiotics should be minimized and, if possible, alternative treatments should be used in order to prevent antibiotic-resistance. An example of such an alternative treatment is replacement of a medical device associated with HAI.

Treatment and prevention of infections associated with *S. epidermidis* is thus particularly challenging due to its presence on skin and mucous membranes taken together with its resistance to antibiotics.

WO 2014/016157 discloses a treatment preparation for treatment of sores, wounds, ulcers or the like, or a fistula or otitis. The preparation comprises hypochlorite and amino acids. The treatment preparation may be prepared from a kit of parts comprising a first aqueous component comprising one or more amino acids, and a second aqueous component comprising an active halogen compound, wherein the pH of the first component and/or the second component is about 9 to 11.5. It is described that the treatment preparation may have antibacterial effects, and that the bacteria against which the treatment preparation is useful may be *staphylococcus*. However, *S. epidermidis* is not mentioned.

Arch Oral Biol. 2012 July; 57(7):940-7 discloses that sodium hypochlorite is effective when tested as an antimicrobial agent on biofilm on titan specimens, but was not recommended for the topical disinfection and detoxification of infected implant surfaces due to possible toxicity and lack of broad-spectrum antimicrobial effect.

The widespread occurrence of infections associated with *S. epidermidis* and the fact that they are difficult to treat cause suffering for patients and high costs for public health care systems. Thus, there remains a need for treatments of infections associated with *S. epidermidis* which do not include the use of antibiotics or reduce the use of antibiotics. Moreover, there is a need for treatment of infections involving *S. epidermidis* which are non-toxic, cause no or few side-effects, are cheap and/or simple to use.

It is an object of the present disclosure to overcome or at least alleviate one or more of the problems discussed above, and/or to provide advantages and aspects not provided by hitherto known techniques.

SUMMARY

The present disclosure provides kit of parts comprising
a) a first component comprising a single amino acid, said single amino acid being leucine, and
b) a second component comprising an active chlorine compound,
wherein the kit of parts comprises no further amino acid in addition to said single amino acid of said first component.

The present disclosure also provides a treatment preparation obtainable by mixing:
a) a first component as described herein, and
b) a second component, as defined herein, and
c) optionally water.

The present disclosure also provides an agent comprising the treatment preparation described herein, wherein said agent is an agent for treating and/or preventing an infection associated with *Staphylococcus Epidermidis*.

The present disclosure also provides
an article treated with the treatment preparation described herein and/or the agent described herein.

Further, the present disclosure also provides
a kit of parts as described herein, or
a treatment preparation or an agent as described herein, or
an agent as described herein
for use as a medicament in therapy.

The present disclosure also provides
a kit of parts as described herein, or
a treatment preparation as described herein, or
an agent as described herein
for use in the treatment and/or prevention of an infection associated with *S. epidermidis*.

The present disclosure also provides a use of
a kit of parts as described herein, or
a treatment preparation as described herein, or
an agent as described herein
for the manufacture of a medicament the treatment and/or prevention of an infection.

The present disclosure also provides a method of treating and/or preventing an infection associated with *S. epidermidis* at a treatments site, said method comprising applying to the treatment site an effective amount of the treatment preparation as described herein, thereby treating and/or preventing the infection associated with *S. epidermidis*.

DESCRIPTION

The present disclosure provides a kit of parts comprising:
a) a first component comprising a single amino acid, said single amino acid being leucine, and
b) a second component comprising an active chlorine compound;
wherein said kit of parts comprises no further amino acid in addition to said single amino acid of said first component.

Thus, the kit of parts contains leucine, and lacks further amino acids. The leucine may be L-leucine and optionally D-leucine. Alternatively, the leucine may be D-leucine.

The present disclosure is based on the unexpected finding that mixing a single amino acid, said amino acid being leucine, with hypochlorite provides a treatment preparation which is more bactericidal as compared to a treatment preparation prepared from three amino acids and hypochlorite. In particular, it has been found that a treatment preparation prepared from leucine and hypochlorite is more bactericidal towards *Staphylococcus epidermidis* than a treatment preparation prepared from leucine, lysine, glutamic acid and hypochlorite.

The two components of the kit of parts are intended to be mixed together and thereby form a treatment preparation. The treatment preparation may be used in the prevention and/or treatment of an infection such as an infection comprising biofilm.

While not wishing to be bound by any specific theory, it is believed that the treatment preparation described herein acts by reducing or eradicating *Staphylococcus epidermidis* and optionally undesired matter such as further bacteria, fungi and/or viruses in or on a treatment site. The mode of action of the treatment preparation described herein may be facilitating debridement of a treatment site. Further, it is believed that the high pH of the treatment preparation beneficially impacts debridement. In particular, it is believed that the high pH observed after mixing of the kit components described herein beneficially impacts mechanical removal of undesired matter in a treatment site as described herein. The treatment preparation described herein may therefore be used as a substance-based medical device.

The second component of the kit of parts comprises an active chlorine compound. The active chlorine compound may be $Cl_2$, chloride, hypochlorite, chlorite, chlorate and/or perchlorate. Alternatively, the active chlorine compound may be $Cl_2$, hypochlorite, chlorite, chlorate, and/or perchlorate. Further, the active chlorine compound may be $Cl_2$ and/or hypochlorite. Further, the active chlorine compound may be hypochlorite.

The active chlorine compound of the second component may comprise or consist of one or more of the following: NaOCl, KOCl, $Ca(OCl)_2$. For example, the second component may comprise or consist of NaOCl. In a further example, the second component may comprise or consist of $Ca(OCl)_2$.

The first component and/or the second component of the kit of parts may be provided in solid form. For instance, the first component and/or second component may be lyophilized. In an example, the first component and the second component may be provided as a solid such as a powder.

Additionally or alternatively, the first component may be an aqueous component and/or the second component may be an aqueous component. Thus, the first and/or second component may comprise water. The pH of the first component and/or the second component may be equal to or above 9 such as within the range of from about 9 to about 11.5.

The kit of parts described herein may further comprise water. The water may be added to the components of the kit of parts described herein.

The first aqueous component may further comprise a gel substance.

The gel substance may comprise or consist of polyethylene glycol (PEG), and/or carboxymethyl cellulose and/or a polysaccharide substance or a salt thereof, such as sodium carboxymethyl cellulose (Na-CMC). For instance, the first component further comprises a gel selected from the group consisting of polyethylene glycol (PEG), carboxymethyl cellulose, a polysaccharide substance, a salt of any of the foregoing gels, and any combination of the foregoing gels and/or salts thereof.

The first component may comprise 2-4% (by weight) gel substance.

The gel substance provides moist keeping means to keep a moist environment for a treatment site of a subject such as a patient, and in particular the gel substance reduces evaporation from the aqueous treatment preparation prepared from the first and second components, when applied to the treatment site. Furthermore, the gel substance also provides a proper consistency to the treatment preparation prepared from the two components.

The first component of the kit of parts described herein may comprise from about 0.1 wt % to about 1 wt % of the single amino acid based on the total weight of the first component. For example, the first component may comprise about 0.20 wt % or about 0.72 wt % of the single amino acid based on the total weight of the first component. Alternatively, the first component of the kit of parts may comprise less than 0.1 wt % of the single amino acid such as from 0.01 to 0.099 wt % of the single amino acid based on the total weight of the first component.

The second component of the kit of parts described herein may comprise from about 0.01 wt % to about 5 wt % such as from about 0.01 to about 1 wt % of the active chlorine compound based on the total weight of the second component. For example, the second component described herein may be present in an amount of about 0.25 wt % or about 0.90 wt % based on the total weight of the second component.

If nothing else is mentioned, percentage by weight herein refers to the weight of a compound or the like relative the total amount of the mentioned component or the like comprising said compound or the like. Percentage by weight is also denominated weight % or wt %. In this document, the expressions "weight %" and "wt %" are used interchangeably. Since the first and/or second components may be aqueous compositions the concentration may also be expressed as density using ww/v, i.e. weight per volume.

The first and/or second component may further comprise NaCl and/or $TiO_2$.

$TiO_2$ may aid in increasing the visibility of the gel as described herein thereby facilitating observing where the gel has been applied.

The presence of NaCl in the treatment preparation described herein is intended to adjust the tonicity of the gel.

The pH of the first aqueous component and/or the second aqueous component described herein may be equal to or above about 9 such as within the range of from about 9 to about 11.5.

The kit of parts may further comprise instructions for use. The instructions may involve instructions for mixing the first component with the second component, how to mix the first and second components into a treatment preparation, how to apply the treatment preparation and/or how often the treatment preparation should be applied. The instructions may also include instructions for adding further components such as the further components described herein.

The components of the kit of parts described herein may be mixed to form a treatment preparation. While not wishing to be bound by any specific theory, it is believed that mixing of the two components of the kit of parts leads to the formation of N-chloro leucine, i.e. leucine carrying one chloro atom on its nitrogen atom, which may subsequently decompose into products that are harmless to a patient such as a human or an animal. It is also believed that mixing of the components to form a treatment preparation leads to release of sodium hydroxide (NaOH).

Thus, there is provided a treatment preparation obtainable by mixing:

a) a first component as described herein, b) a second component as described herein, and c) optionally water.

Thus, the treatment preparation may be prepared from the kit of parts described herein. The pH of the treatment preparation may be greater than the pH of the first component and/or the second component. Further, this greater pH of the treatment preparation may be maintained for a time period such as a time period from about one minute to about five minutes by the absence of mixing such as stirring the treatment preparation. Thus, following mixing of the first and second components there may be no or substantially no mixing such as stirring.

The treatment preparation may be a treatment preparation in solid form such as a powder or it may be an aqueous treatment preparation.

When both components are in aqueous form the combination of the first aqueous component and the second aqueous component will provide the treatment preparation as an aqueous treatment preparation.

The first and second aqueous components may be mixed in the volume ratios of 1:2 to 2:1, preferably about 1:1, thereby forming the treatment preparation for use in the treatment and/or prevention of an oral and/or non-oral bacterial infection as described herein.

The treatment preparation may also be prepared by mixing one of the components in solid form with the other component in aqueous form. Optionally, water may be added to e.g. facilitate mixing of the components and/or adjust the consistency of the treatment preparation being produced. For example, the treatment preparation may be prepared from a first aqueous component described herein and a second component in solid form as described herein. In a further example, the treatment preparation may be prepared from a first component in solid form as described herein and a second aqueous component as described herein.

When both the first component and the second component are provided in solid form they may be kept separately or together. In the latter case, the first component and second component form a solid treatment preparation which upon mixing with water provides the treatment preparation described herein.

At room temperature (i.e. about 20 degrees Celsius) and 1 atm of pressure (i.e. about 101325 Pa), and within 30 seconds after the components have been mixed together, the pH of the aqueous treatment preparation may be equal to or above about 9. For instance, the pH may be within the range of from about 9 to about 13.

It has been observed that pH increases upon mixing of the components of the kit described herein. In particular, pH increases just after mixing of the components. The high pH is believed to have a beneficial impact on the softening of matter of the treatment site thereby facilitating removal of said matter. The matter being removed may be necrotic tissue. As used herein, debridement intends removal of undesired matter such as necrotic tissue and/or devitalized tissue. Thus, the high pH is believed to have a beneficial impact on softening undesired matter such as necrotic tissue thereby facilitating debridement of a treatment site such as a wound, a sore and/or an implant surface. Thus, the effect of the high pH is believed to be mechanical. It has been found that the high pH observed after mixing of the first and second components is maintained for about five minutes. Therefore, incubation of the treatment site with the treatment preparation for about five minutes is believed to have a beneficial effect on the treatment.

The treatment preparation may be prepared immediately prior to being applied to a treatment site, such as within two minutes prior to being applied to the treatment site. Additionally or alternatively, the first component and second components may be applied and mixed directly on the treatment site thereby forming the treatment preparation on the treatment site.

The treatment preparation described herein may be applied to a treatment site which may be a treatment site of a patient such as a human or animal, or a treatment site of a medical device and/or instrument. The treatment site described herein may be an oral treatment site and/or a non-oral treatment site. The treatment site may involve an infection as described herein. For example, the oral treatment site may be tooth dentine tissue such as carious tooth dentine tissue, tissues surrounding a tooth or a tooth implant and/or the surface of a tooth or a tooth implant. Examples of a non-oral treatment site include a sore, wound, burn, ulcer, fistula and/or otitis, which may or may not involve Health-Care Associated Infection.

The treatment preparation described herein may be applied to the treatment site once or several times during the same treatment session and/or during separate treatment sessions. Thus, the treatment preparation may be administrated to the treatment site repeatedly. For instance, examination of the treatment site may reveal if it is suitable to add the treatment preparation once or repeatedly. The examination may be visual inspection. The examination may be made with respect to bleeding on probing, the degree of swelling and/or colour of the tissues involved, etc. The skilled person, such as a doctor or a dentist, will be able to determine which time interval between the treatments is appropriate, i.e. how often the treatment preparation should be applied. As an example, the time interval between treatments may be one, two, three, four, five, six weeks, or more.

As described herein, the treatment preparation described herein is believed to facilitate removal of undesired matter thereby shortening the treatment time. This may be seen as a debridement of the treatment site. Thus, the treatment preparation described herein may be a debridement agent such a wound debridement agent and/or a sore debridement agent.

Moreover, the treatment preparation described herein has been shown to have a very good antibacterial effect, such as a good effect on reducing or eradicating *Staphylococcus epidermidis*. In particular, the antibacterial effect of the treatment preparation described herein has been found to be superior to use of an aqueous hypochlorite solution. Advantageously, the treatment preparation described herein is less aggressive towards mucous membranes than an aqueous hypochlorite solution.

The treatment preparation described herein has also been shown to be more bactericidal than a treatment preparation prepared from leucine, lysine, glutamic acid and hypochlorite, and also more bactericidal than a treatment preparation prepared from lysine and hypochlorite. Thus, the treatment preparation described herein advantageously allows for reducing the number of substances involved and yet improves the bactericidal effect. Further, any products resulting from decomposition of N-chloro leucine are harmless to humans.

The treatment preparation described herein may be used alone or in combination with a further treatment or therapy. In the latter case, the combination with a further treatment or therapy may be considered adjunctive therapy. The further treatment or therapy may involve a pharmaceutical drug, a substance-based medical device and/or a wound dressing.

Thus, there is provided an agent comprising or consisting of the treatment preparation described herein. The agent may be one or more of the following: a biofilm softening and/or removal agent, a biofilm eradicator a disinfectant, a cleansing agent, an agent for treating atopic dermatitis, a debridement agent such as a wound debridement agent, sore debridement agent, an agent for treating Health-Care Associated Infection. In particular, the agent may be a debridement agent such as a sore and/or wound debridement agent.

The treatment preparation and/or the agent described herein may be used for treating one or more of the following: dentine caries, a gum infection, an infection associated with an implant, atopic dermatitis, an infection associated with a non-oral treatment site selected from the group consisting of a sore, a wound, a burn, an ulcer, a fistula and otitis. The gum infection may comprise or consist of gingivitis and/or periodontitis. The implant may be a dental implant or a non-dental implant. The non-dental implant, which may also be denominated a prosthesis, may be one or more of the following: an orthopaedic implant, a cochlear implant, a cardiovascular implant such as a heart valve, a contraceptive implant, an urological implant. The non-dental implant may be integrated with or within the body of a patient. Further, the non-dental implant may be permanently implanted or removable. The sore may be a diabetic foot sore and/or a bedsore. The infection associated with an implant such as a dental implant may be peri-implantitis or oral mucositis.

In many applications it is desired to reduce the presence of microorganisms such as bacteria on the equipment involved prior or just prior to use. In this way, infections are prevented from occurring. Commonly, a disinfectant agent and/or an autoclave is/are used to achieve this.

Advantageously, the treatment preparation described herein may be used for disinfecting an article. The article may be a dental article and/or a medical article. The dental article may be a dental device such as a dental implant or a dental instrument. The medical article may be a medical device such as a non-dental implant or a medical instrument. In a further example, the article may be equipment in industry. For example, the article described herein may be a dental implant or a non-dental implant. In a further example, the article may be a medical device such as a catheter or a prosthetic implant.

Thus, there is provided an article such as an article described herein treated with the treatment preparation described herein. The article may be a medical device such as a dental implant or a non-dental implant such as a prosthetic implant.

There present disclosure also provides
a kit of parts as described herein, or
a treatment preparation as described herein, or
an agent as described herein
for use as a medicament in therapy.

Further, the present disclosure provides
a kit of parts as described herein, or
a treatment preparation as described herein or
an agent as described herein
for use in the treatment and/or prevention of an infection associated with *S. epidermidis*.
The present disclosure also provides a use of
a kit pf parts as described herein, or
a treatment preparation as described herein or
an agent as described herein
for the manufacture of a medicament for the treatment and/or prevention of an infection associated with *S. epidermidis*.

The present disclosure also provides a method of treating and/or preventing an infection associated with *S. epidermidis* at a treatment site, said method comprising applying to a treatment site an effective amount of a treatment preparation as described herein or an agent as described herein thereby treating and/or preventing the infection associated with *S. epidermidis*. The treatment site may be a treatment site of a subject such as a human or an animal. The subject may have been diagnosed with the infection associated with *S. epidermidis*. Further, the treatment site may be a topical treatment site such as a topical infection treatment site. Additionally or alternatively, the treatment site may be an article or medical device as described herein such as a surface of said article or medical device. The infection associated with *S. epidermidis* may be as described herein.

In the method described herein, the first component and the second component may be applied to the treatment site simultaneously thereby providing a treatment preparation on the treatment site. Alternatively, the first component and the second component may be applied to the treatment site sequentially thereby providing a treatment preparation on the treatment site. It is believed that the absence of mixing is beneficial for maintaining a high pH, such a s pH above the pH of the first component and/or the second component, in the treatment preparation on the treatment site. Further, no mixing of the treatment site may take place after application to the treatment site. Incubation of the treatment preparation applied to the treatment site may take place for about five minutes.

The infection associated with *S. epidermidis* described herein may be a Health-Care Associated Infection, a wound, sore, an ulcer, a burn and/or a fistula such as an anal fistula. Further, the infection associated with *S. epidermidis* may be an oral infection or a non-oral infection. As used herein, an oral infection takes place in the oral cavity while a non-oral infection takes place in or on the body of a patient such as a human or an animal. Additionally or alternatively, the infection associated with *S. epidermidis* may involve biofilm such as a biofilm involving *S. epidermidis* and optionally further pathogens.

In this document, a Health-Care Associated Infection intends an infection acquired by a patient in connection with medical care. Examples of Health-Care Associated Infections include catheter-associated urinary tract infection (CAUTI), central line associated bloodstream infection (CLABSI), surgical site infection (SSI) and ventilator-associated events (VAE). Further, wounds, sores, ulcers and/or burns may be associated with Health-Care Associated Infection. It will be appreciated that the wounds, sores, ulcers and/or burns described herein may or may not be associated with a Health-Care Associated Infection.

The infection described herein may be selected from the group consisting of dentine caries, a gum infection, an infection associated with an implant an infection associated with a non-oral treatment site selected from the group consisting of a sore, a wound, a burn, an ulcer, a fistula and otitis. The gum infection may comprise or consist of gingivitis and/or periodontitis. The implant may be a dental implant or a non-dental implant. The non-dental implant may be one or more of the following: an orthopaedic implant, a cochlear implant, a cardiovascular implant such as a heart valve, a contraceptive implant, an urological implant. The infection associated with a dental implant may be peri-implantitis or oral mucositis. The sore may be a diabetic foot sore and/or a bedsore. The infection associated with an implant such as a dental implant may be peri-implantitis or oral mucositis. The infection described herein may be an infection of a fistula such an anal fistula. Further, the infection described herein may be chronic.

Oral Infections

The treatment preparation described herein may be used for treating an oral infection such as carious dentine, gum disease, oral mucositis and/or peri-implantitis.

Carious dentine involves dental caries taking place in the dentine tissue of a tooth. Carious dentine is commonly harder to detect by the naked eye than enamel caries. The dentist usually uses a dental instrument to find out if the dentine tissue is soft, which indicates that caries is present. Additionally or alternatively, a dye such as a hydrazine derivative may be used to stain dentine tissue that is affected by caries.

Gum disease, which may also be called periodontal disease, is a disease involving the periodontum (i.e the gums supporting the teeth).

Oral mucositis, which may also be called peri-implant mucositis, is a reversible inflammatory change of the soft tissues surrounding a dental implant without concomitant bone loss. Generally, oral mucositis is a stage preceding peri-implantitis.

Peri-implantitis is a localized lesion involving bone loss around an osseointegrated dental implant, i.e. a dental implant that is directly connected to the bone surrounding it without intervening soft tissue. Further, the peri-implant pockets and/or tissues surrounding the dental implant may be swollen and/or involved in inflammation and/or infection.

Non-Oral Infections

The treatment preparation described herein may be used for treating a non-oral infection such as a sore, wound, burn, ulcer, fistula, otitis and/or atopic dermatitis. The infection may be chronic. Further, the infection may comprise pus and/or necrotic parts.

Examples of sores that may be treated using the treatment preparation described herein include chronic sores, bedsores, diabetic foot sores, and vasculitis sores.

Examples of wounds that may be treated using the treatment preparation described herein may be open wounds. The wound may be caused by injury.

Example of ulcers that may be treated using the treatment preparation described herein include skin ulcers. Skin ulcers are sores wherein tissues disintegrate and may result in loss of epidermis, dermis and even subcutaneous tissue.

A fistula is a connection or passage between two organs that usually do not connect. Examples of fistulas that may be treated using the treatment preparation described herein include anal fistulas and urinary tract fistulas.

Atopic dermatitis, which is also known as atopic eczema, is a type of inflammation of the skin (i.e. dermatitis). Atopic dermatitis (AD) is characterized by an increased susceptibility to skin infections. *Staphylococcus aureus* is reported to dominate in AD lesions and reports have revealed the presence of staphylococcal biofilms.

The invention is further illustrated by the following non-limitative Examples.

EXAMPLES

The killing effect on vegetative bacteria (*Staphylococcus epidermidis* ATCC 14990) was evaluated in these Examples. The bacterial effect on Staph. *epidermidis* was evaluated and compared for four formulations when using a contact time of five minutes.

Material

In the experiments below the following products were used: Perisolv, Reference Product, Leucine Product and Lysine Product. The products were kept at from +2° C. to +8° C. prior the test execution. Tween 80 is a nonionic surfactant and emulsifier. Cfu stands for colony forming units. Milliliters are denoted "ml" or "mL". In all experiments, component 1 and component 2 were mixed just prior to use. Component 1 and component 2 were mixed in a 1:1 volume ratio. In this document, the L form of the amino acid was used unless otherwise indicated.

Perisolv

The product Perisolv consisted of two separate components: Component 1 and Component 2, which were mixed prior to use. The amounts of the components of Perisolv were as indicated in Table 1 below.

TABLE 1

| Component | Amounts of Component 1 | Amounts of Component 2 |
|---|---|---|
| Water, highly purified | Up to 100 wt % | Up to 100 wt % |
| Carboxymethylcellulose Sodium (CMC) | 2-4% | — |
| Amino acids (glutamic acid, leucine, lysine) | 0.4-0.8* wt % | — |
| Sodium Chloride NaCl | 0.3-0.6 wt % | — |
| Titanium dioxide TiO$_2$ | 0.03-0.1 wt % | — |
| Sodium hypochlorite NaOCl | — | 1-2 wt % |
| NaOH | Added in an amount providing a pH from 9 to 11.5 | |
| Aqueous HCl | | Added in an amount providing a pH from 9 to 11.5 |

*Total amount of amino acids, the amino acids being present in a relation by weight of about 1:1:1

Reference Product

The reference product consisted of two separate components: Component 1 and Component 2, which were mixed prior to use. The amounts of the components of the Reference Product were as indicated in Table 2 below.

TABLE 2

| Component | Amounts of Component 1 | Amounts of Component 2 |
|---|---|---|
| Water, highly purified | Up to 100% | Up to 100% |
| Carboxymethylcellulose Sodium (CMC) | 2-4 wt % | |
| Amino acids (glutamic acid, leucine, lysine)* | — | |
| Sodium Chloride NaCl | 0.3-0.6 wt % | |

TABLE 2-continued

| Component | Amounts of Component 1 | Amounts of Component 2 |
|---|---|---|
| Titanium dioxide TiO$_2$ | 0.03-0.1 wt % | |
| Sodium hypochlorite NaOCl | — | 1-2 wt % |
| NaOH | Added in an amount providing a pH from 9 to 11.5 | |
| Aqueous HCl | | Added in an amount providing a pH from 9 to 11.5 |

Leucine Product

The Leucine Product consisted of two separate components: Component 1 and Component 2, which were mixed prior to use. The amounts of the Leucine Product were as indicated in Table 3 below. As shown in Table 3, the only amino acid present in the Leucine Product was leucine.

TABLE 3

| Component | Amounts of Component 1 | Amounts of Component 2 |
|---|---|---|
| Water, highly purified | Up to 100 wt % | Up to 100 wt % |
| Carboxymethylcellulose Sodium (CMC) | 2-4 wt % | — |
| Amino acid (leucine)* | 0.4-0.8 wt % | — |
| Sodium Chloride NaCl | 0.3-0.6 wt % | — |
| Titanium dioxide TiO$_2$ | 0.03-0.1 wt % | — |
| Sodium hypochlorite NaOCl | — | 1-2 wt % |
| NaOH | Added in an amount providing a pH from 9 to 11.5 | |
| Aqueous HCl | | Added in an amount providing a pH from 9 to 11.5 |

Lysine Product

The Lysine Product consisted of two separate components: Component 1 and Component 2, which were mixed prior to use. The amounts of the Lysine Product were as indicated in Table 4 below. As shown in Table 4, the only amino acid present in the Lysine Product was lysine.

TABLE 4

| Component | Amounts of Component 1 | Amounts of Component 2 |
|---|---|---|
| Water, highly purified | Up to 100 wt % | Up to 100 wt % |
| Carboxymethylcellulose Sodium (CMC) | 2-4 wt % | — |
| Amino acid (lysine)* | 0.4-0.8 wt % | — |
| Sodium Chloride NaCl | 0.3-0.6 wt % | — |
| Titanium dioxide TiO$_2$ | 0.03-0.1 wt % | — |
| Sodium hypochlorite NaOCl | — | 1-2 wt % |
| NaOH | Added in an amount providing a pH from 9 to 11.5 | Added in an amount providing a pH from 9 to 11.5 |
| Aqueous HCl | | Added in an amount providing a pH from 9 to 11.5 |

Comment Regarding Perisolv, the Reference Product, the Leucine Product and the Leucine Product Perisolv, the Reference product, the Leucine Product and the Leucine Product all contained the same amount of CMC, NaCl, TiO$_2$ and NaOCl.

Perisolv, the Leucine Product and the Lysine product all contained the same total amount of amino acid(s). In this document, a hyphen, i.e. "-", means 0 percent by weight (wt %).

Microorganism Preparation

The bacterium *Staphylococcus epidermidis* ATCC14990 was inoculated on Tryptone Soy Agar (TSA) plates from a thawed stock solution. After incubation, single colonies were transferred to tubes with a solution of 0.9% NaCl and 0.1% Tween 80, and mixed to a light turbidity. The suspension was diluted in a 10-fold step dilution series and tested immediately in duplicates by a surface spread method.

The plates were incubated overnight and the suspension was stored in refrigerator and used in a test within 24 hours. The concentration was calculated and adjusted to approximately 10$^8$ cfu/mL.

Media Used in the Test

Neutralizing buffer—0.075 M phosphate buffer with 0.3% lecithin, 3.0% Tween 80, 0.5% sodium thiosulfate, and 0.1% L-histidine.

TSA (Soybean-casein digest agar) plates.

Testing of the Killing Effect on the Bacteria *Staphylococcus epidermidis* ATCC 14990

In Examples 1~4 below the killing effect on the bacteria *Staphylococcus epidermidis* ATCC 14990 of the products identified above (i.e. Perisolv, the Reference Product, the Leucine product and the Lysine Product) was evaluated. It is noted that the bacteria *Staphylococcus epidermidis* ATCC 14990 is a bacteria that is found inter alia in the context of periimplant associated diseases such as peri-implantitis and also in the context of wounds, sores etc. Bacterial cells were added at a concentration of about 10$^7$ cfu/mL to the product and the reducing effect was evaluated after 5 minutes.

Furthermore, a negative control was also used. Two bottles of neutralizing buffer were tested as negative controls with no growth after 7 days of incubation.

The experiments were performed in room temperature. All media used were tempered in the laboratory for >1 hour prior to the test, while the product was kept at 30-35° C. until used.

Example 1

The components of Perisolv were mixed. Immediately after the mixing, 10$^7$ cfu of *Staphylococcus epidermidis* was added to 5 mL of the Perisolv product, in duplicates.

The resulting mixture was allowed to stand for 5 minutes, and thereafter the samples were mixed and 0.1 mL of the sample was added to 50 mL of neutralizing buffer. The solution was analyzed by filtrating fractions corresponding to 10-fold step dilutions. Each sample was filtered and filters were rinsed once with 100 mL of 0.9% NaCl before incubated on TSA plates at 30-35° C. for 3 days.

For enumeration of the bacteria, 10$^7$ cfu of the microorganism were added to a bottle of neutralizing buffer in duplicates without the product (i.e. a positive control sample). The filtration was performed as above.

The reduction of microorganism was calculated as the log$_{10}$ of the surviving microorganisms and compared to that of the enumeration (i.e. the positive control sample).

Example 2

This example was performed in analogy with Example 1, but the Reference Product was used instead of Perisolv.

Example 3

This example was performed in analogy with Example 1, but the Leucine Product was used instead of Perisolv.

Example 4

This example was performed in analogy with Example 1, but the Lysine Product was used instead of Perisolv.

Results

Below the results of viable count of test microorganism (i.e. *Staphylococcus epidermidis* ATCC4990) in a product tested (see Examples 1-4) with 5 minutes of contact time and $log_{10}$ reduction of the microorganisms relative to $log_{10}$ of the positive control of the microorganism is presented. $Log_{10}$ reduction was calculated from the mean value of the viable count in the product tested. The results of Examples 1-4 are shown in Table 5 below.

TABLE 5

| Product tested | Viable count product, mean value (cfu/mL) [1] | Logarithmic reduction of the number of *Staphylococcus epidermidis* ATCC 14990 |
|---|---|---|
| Perisolv | 10 | 5.1 |
| Reference product | 35 | 4.6 |
| Leucine Product | <10 | >5.1 |
| Lysine Product | 55 | 4.4 |

[1] The detection limit is 10 cfu/mL, thus 0 cfu is presented as <10.

As shown in Table 5, the Leucine Product was found to be more efficient in the killing of the bacteria than Perisolv, the Reference Product and the Lysine Product. Further, the Lysine Product was found to be less efficient in the killing of the bacteria than Perisolv, the Reference Product and the Leucine Product.

Thus, the Leucine Product allows for treating infections involving bacteria.

Example 5A

This experiment was performed in order to see if there was a difference in bactericidal effect between L-leucin and D-leucin. The composition of L-leucin and D-leucin products were as indicated in Table 6 below. For the experiment Component 1 and Component 2 were mixed prior to use.

TABLE 6

| Component | Amounts of Component 1 | Amounts of Component 2 |
|---|---|---|
| Water, highly purified | Up to 100 wt % | Up to 100 wt % |
| Carboxy-methylcellulose Sodium (CMC) | 2-4 wt % | — |
| Amino acid (L or D leucine) | 0.2-0.8 wt % | — |
| Sodium Chloride NaCl | 0.3-0.6 wt % | — |
| Titanium dioxide TiO$_2$ | 0.03-0.1 wt % if present | — |
| Sodium hypochlorite NaOCl | — | 0.90 wt % |

TABLE 6-continued

| Component | Amounts of Component 1 | Amounts of Component 2 |
|---|---|---|
| NaOH | Added in an amount providing a pH from 9 to 11.5 | |
| Aqueous HCl | | Added in an amount providing a pH from 9 to 11.5 |

The L-Leucine product and the D-Leucin products were tested on *Staphylococcus* A and *Staphylococcus* E in analogy with Example 1. The results are shown in Table 7 below.

TABLE 7

| Product tested | Logarithmic reduction of the number of *Staphylococcus A* | Logarithmic reduction of the number of *Staphylococcus E* |
|---|---|---|
| L-Leucine product TiO$_2$ was present | 4.6 | 4.4 |
| D-Leucine product TiO$_2$ was present | >5.0 | 4.8 |
| L-Leucine product without TiO$_2$ present | >5.0 | >4.8 |

Example 5B

Example 5B was performed in analogy with Example 5A, but the concentration of sodium hypochlorite was 0.25 wt % instead of 0.90 wt %. The results are shown in Table 8 below.

TABLE 8

| Product tested | Logarithmic reduction of the number of *Staphylococcus A* | Logarithmic reduction of the number of *Staphylococcus E* |
|---|---|---|
| L-Leucine product TiO$_2$ was present | 4.2 | >4.8 |
| D-Leucine product TiO$_2$ was present | 4.2 | >4.8 |
| L-Leucine product without TiO$_2$ present | >5.0 | 4.0 |

From Examples 5A and 5B it was concluded that both the L-Leucine product and the D-Leucine product had a bactericidal effect.

The invention claimed is:

1. A method of treating and/or preventing an infection at a treatment site, said method comprising applying to the treatment site an effective amount of the treatment preparation comprising:
   a) a first component comprising a single amino acid, said single amino acid being leucine,
   b) a second component comprising an active chlorine compound, wherein the active chlorine compound is selected from the group consisting of Cl$_2$, chloride, hypochlorite, chlorite, chlorate, and perchlorate, and
   c) optionally water,
   wherein the method comprises no further amino acid in addition to said single amino acid being leucine of said first component,
   thereby treating and/or preventing the infection.

2. The method according to claim 1, wherein the treatment site is a treatment site of a subject.

3. The method according to claim 2, wherein the treatment site is a topical treatment site.

4. The method according to claim 1, wherein the treatment site is a medical device.

5. The method according to claim 1, wherein the infection is one or more of the following: a Health-Care Associated infection, a wound, a sore, an ulcer, a burn, a fistula.

6. The method according to claim 2 wherein the subject has been diagnosed with the infection associated with *S. epidermidis*.

7. The method according to claim 1, wherein the first component and the second component are applied to the treatment site simultaneously thereby providing a treatment preparation on said treatment site.

8. The method according to claim 1, wherein the first component and the second component are applied to the treatment site sequentially thereby providing a treatment preparation on said treatment site.

9. The method according to claim 1, wherein no mixing of the treatment preparation takes place after application of the first and second components to the treatment site.

10. The method according to claim 1, wherein the method comprises incubation of the treatment preparation applied to the treatment site.

11. The method according to claim 1, wherein the leucine is L-leucine.

12. The method according to claim 1, wherein the leucine is D-leucine.

13. The method according to claim 1, wherein said first component and/or said second component is/are provided in solid form.

14. The method according to claim 1, wherein the first component further comprises NaCl and/or $TiO_2$.

15. The method according to claim 1, wherein the active chlorine compound of the second component is one or more of the following: NaOCl, KOCl, $Ca(OCl)_2$.

16. The method according to claim 1, wherein said first component further comprises a gel selected from the group consisting of polyethylene glycol (PEG), a polysaccharide substance, a salt of any of the foregoing gels, and any combination of the foregoing gels and/or salts thereof.

17. The method according to claim 1, wherein the first component comprises from 0.1 wt % to 1 wt % of the single amino acid based on the total weight of said first component, and/or the second component comprises from 0.01 wt % to 5 wt % of the active chlorine compound based on the total weight of said second component.

18. The method according to claim 5, wherein the sore is a diabetic foot sore.

19. The method according to claim 5, wherein the sore is a bedsore.

20. The method according to claim 5, wherein the infection is a burn.

21. The method according to claim 1, wherein said first component further comprises a gel of carboxymethyl cellulose, or a salt thereof, or a combination thereof.

* * * * *